(12) United States Patent
Mogensen et al.

(10) Patent No.: US 11,617,827 B2
(45) Date of Patent: *Apr. 4, 2023

(54) INVISIBLE NEEDLE (71) Applicant: UnoMedical A/S, Lejre (DK)

(72) Inventors: Lasse W. Mogensen, Søborg (DK); Orla Mathiasen, Sørø (DK)

(73) Assignee: Unomedical A/S, Lejre (DK)

( * ) Notice: Subject to any disclaimer, the term of this patent is extended or adjusted under 35 U.S.C. 154(b) by 837 days.

This patent is subject to a terminal disclaimer.

(21) Appl. No.: 16/530,926

(22) Filed: Aug. 2, 2019

(65) Prior Publication Data
US 2019/0351137 A1 Nov. 21, 2019

Related U.S. Application Data (63) Continuation of application No. 11/519,137, filed on Sep. 11, 2006, now Pat. No. 10,369,277.
(Continued)

(30) Foreign Application Priority Data

Sep. 12, 2005 (EP) ..................................... 05019774

(51) Int. Cl.
*A61M 5/158* (2006.01)
*A61M 5/32* (2006.01)
*A61M 39/02* (2006.01)

(52) U.S. Cl.
CPC ............. *A61M 5/158* (2013.01); *A61M 5/326* (2013.01); *A61M 39/02* (2013.01);
(Continued)

(58) Field of Classification Search
CPC ...... A61M 5/158; A61M 5/326; A61M 39/02; A61M 2005/1581; A61M 2005/1585; A61M 2005/1587; A61M 25/0612
See application file for complete search history.

(56) References Cited

U.S. PATENT DOCUMENTS 10,071,210 B2    9/2018 Gray
10,292,641 B2    5/2019 Bureau et al.
(Continued)

FOREIGN PATENT DOCUMENTS

EP    3257533 A1    12/2017
EP    3305349 A1    4/2018
(Continued)

*Primary Examiner* — Theodore J Stigell
(74) *Attorney, Agent, or Firm* — Taft Stettinius & Hollister LLP; Ryan O. White; Derek B. Lavender (57) ABSTRACT The invention relates to an inserter for an infusion set for intermittent or continuous administration of a therapeutical substance, such as e.g. insulin. The inserter comprises a needle hub comprising an insertion needle and two spring units assuring automatic insertion and automatic retraction of the insertion needle.
The inserter comprises a housing (1), a carrier body (2) carrying an infusion part (8), a needle hub (3), a first moving unit (4) bringing the carrier body (2) to a forward position and a second moving unit (5) bringing the carrier body (2) to a retracted position. The inserter is characterized in that it has means for activation which should be activated at least once in order to bring the carrier body (2) from a retracted to a forward position, and back from the forward to the retracted position.

22 Claims, 5 Drawing Sheets

Related U.S. Application Data (60) Provisional application No. 60/716,222, filed on Sep. 12, 2005.

(52) U.S. Cl.
CPC ............. *A61M 2005/1581* (2013.01); *A61M 2005/1585* (2013.01); *A61M 2005/1587* (2013.01)

(56) References Cited

U.S. PATENT DOCUMENTS

| | | |
|---|---|---|
| 10,293,101 B2 | 5/2019 | Brewer et al. |
| 10,369,274 B2 | 8/2019 | O'Connor et al. |
| 10,369,277 B2 * | 8/2019 | Mogensen ............ A61M 5/158 |
| 10,369,289 B2 | 8/2019 | Cabiri et al. |
| 10,376,638 B2 | 8/2019 | Levesque et al. |
| 10,413,661 B2 | 9/2019 | Kamen et al. |
| 10,432,403 B2 | 10/2019 | Moskal |
| 10,434,245 B2 | 10/2019 | Yodfat et al. |
| 10,434,247 B2 | 10/2019 | Cole et al. |
| 10,434,248 B1 | 10/2019 | Penake et al. |
| 10,434,253 B2 | 10/2019 | DiPerna et al. |
| 10,434,285 B2 | 10/2019 | Schoonmaker et al. |
| 10,438,696 B2 | 10/2019 | Shapley et al. |
| 10,441,356 B2 | 10/2019 | Zarins et al. |
| 10,441,713 B1 | 10/2019 | Feldman et al. |
| 10,441,718 B2 | 10/2019 | Tchao et al. |
| 10,441,723 B2 | 10/2019 | Nazzaro |
| 10,441,775 B2 | 10/2019 | Schriver et al. |
| 10,449,290 B2 | 10/2019 | Shapley et al. |
| 10,449,291 B2 | 10/2019 | Hadian et al. |
| 10,449,296 B2 | 10/2019 | Kapas et al. |
| 10,449,306 B2 | 10/2019 | Grover et al. |
| 10,463,572 B2 | 11/2019 | Shor et al. |
| 10,463,785 B2 | 11/2019 | Dewey |
| 10,463,787 B2 | 11/2019 | Shor et al. |
| 10,463,791 B2 | 11/2019 | Shergold et al. |
| 10,471,203 B2 | 11/2019 | Chappel et al. |
| 10,471,206 B2 | 11/2019 | Dittrich |
| 10,478,550 B2 | 11/2019 | Hadvary et al. |
| 10,478,552 B2 | 11/2019 | Cronenberg et al. |
| 10,478,554 B2 | 11/2019 | Bazargan et al. |
| 10,478,555 B2 | 11/2019 | Radojicic |
| 10,481,024 B2 | 11/2019 | Wade et al. |
| 10,483,000 B2 | 11/2019 | Saint et al. |
| 10,485,923 B2 | 11/2019 | Schiendzielorz |
| 10,485,926 B2 | 11/2019 | Vanderveen et al. |
| 10,485,937 B2 | 11/2019 | Yodfat et al. |
| 10,489,617 B2 | 11/2019 | Salem et al. |
| 10,493,201 B2 | 12/2019 | Cole et al. |
| 10,493,202 B2 | 12/2019 | Hayter |
| 10,493,203 B2 | 12/2019 | Yodfat et al. |
| 10,500,352 B2 | 12/2019 | Grant et al. |
| 10,507,316 B2 | 12/2019 | Fielder et al. |
| 10,512,724 B2 | 12/2019 | Renstad et al. |
| 10,525,193 B2 | 1/2020 | Schauderna |
| 10,525,247 B2 | 1/2020 | Bellrichard et al. |
| 10,532,150 B2 | 1/2020 | Bazargan et al. |
| 10,532,151 B2 | 1/2020 | Wei |
| 10,532,155 B2 | 1/2020 | Schiendzielorz |
| 10,532,159 B2 | 1/2020 | Tornsten et al. |
| 10,532,835 B2 | 1/2020 | Chong et al. |
| 10,537,681 B2 | 1/2020 | Tan-Malecki et al. |
| 10,539,481 B2 | 1/2020 | Plahey et al. |
| 10,542,921 B2 | 1/2020 | Kuhn |
| 10,542,936 B2 | 1/2020 | Goldberg et al. |
| 10,549,029 B2 | 2/2020 | Agard et al. |
| 10,549,033 B2 | 2/2020 | Shimizu |
| 10,549,034 B2 | 2/2020 | Eggert et al. |
| 10,549,036 B2 | 2/2020 | Starkweather et al. |
| 10,549,079 B2 | 2/2020 | Burton et al. |
| 10,556,059 B2 | 2/2020 | Cross et al. |
| 10,556,063 B2 | 2/2020 | Murphy, Jr. et al. |
| 10,561,785 B2 | 2/2020 | Roy et al. |
| 10,561,788 B2 | 2/2020 | Roy |
| 10,561,789 B2 | 2/2020 | Mastrototaro et al. |
| 10,561,826 B2 | 2/2020 | Amano et al. |
| 10,561,831 B2 | 2/2020 | Kato |
| 10,569,011 B2 | 2/2020 | Dilanni et al. |
| 10,569,012 B2 | 2/2020 | Schabbach et al. |
| 10,569,014 B2 | 2/2020 | Hanson et al. |
| 10,576,199 B2 | 3/2020 | Sealfon et al. |
| 10,576,203 B2 | 3/2020 | Amon et al. |
| 10,576,204 B2 | 3/2020 | Estes et al. |
| 10,583,241 B2 | 3/2020 | Wu et al. |
| 10,583,247 B2 | 3/2020 | Mandro |
| 10,589,023 B2 | 3/2020 | Cindrich et al. |
| 10,589,028 B2 | 3/2020 | Cabiri et al. |
| 10,596,317 B2 | 3/2020 | Nakanishi |
| 10,596,362 B2 | 3/2020 | Fielder et al. |
| 10,610,638 B2 | 4/2020 | Cabiri et al. |
| 10,610,639 B2 | 4/2020 | Cabiri et al. |
| 10,610,644 B2 | 4/2020 | Mazlish et al. |
| 10,617,817 B2 | 4/2020 | Hwang et al. |
| 10,617,820 B2 | 4/2020 | O'Connor et al. |
| 10,625,016 B2 | 4/2020 | Amon et al. |
| 10,625,017 B2 | 4/2020 | Searle et al. |
| 10,625,018 B2 | 4/2020 | Destefano et al. |
| 10,632,248 B2 | 4/2020 | Stefanov et al. |
| 10,632,249 B2 | 4/2020 | Marbet et al. |
| 10,632,253 B2 | 4/2020 | Uchiyama et al. |
| 10,632,256 B2 | 4/2020 | Sasaki |
| 10,632,257 B2 | 4/2020 | Estes et al. |
| 10,635,784 B2 | 4/2020 | Rubalcaba, Jr. et al. |
| 10,639,417 B2 | 5/2020 | Roberts |
| 10,639,418 B2 | 5/2020 | Kamen et al. |
| 10,639,661 B2 | 5/2020 | Fontana |
| 10,646,643 B2 | 5/2020 | Cabiri et al. |
| 10,646,652 B2 | 5/2020 | McCullough et al. |
| 10,646,653 B2 | 5/2020 | Despa et al. |
| 10,653,828 B2 | 5/2020 | Brown et al. |
| 10,653,829 B2 | 5/2020 | Barchen et al. |
| 10,653,833 B2 | 5/2020 | Kamen et al. |
| 10,653,835 B2 | 5/2020 | Dobbles et al. |
| 10,653,846 B2 | 5/2020 | Weibel et al. |
| 10,656,894 B2 | 5/2020 | Fryman |
| 10,661,006 B2 | 5/2020 | Antonio et al. |
| 10,661,007 B2 | 5/2020 | Estes |
| 10,661,008 B2 | 5/2020 | Brewer et al. |
| 10,661,067 B2 | 5/2020 | Kodama |
| 10,668,209 B2 | 6/2020 | Montalvo et al. |
| 10,668,210 B2 | 6/2020 | Kamen et al. |
| 10,668,213 B2 | 6/2020 | Cabiri |
| 10,668,227 B2 | 6/2020 | Caspers |
| 10,675,055 B2 | 6/2020 | Chong et al. |
| 10,675,333 B2 | 6/2020 | Ning et al. |
| 10,675,404 B2 | 6/2020 | Pizzochero et al. |
| 10,682,458 B2 | 6/2020 | Wu et al. |
| 10,682,460 B2 | 6/2020 | Adams et al. |
| 10,682,461 B2 | 6/2020 | Oakes |
| 10,682,463 B2 | 6/2020 | Kamen et al. |
| 10,685,749 B2 | 6/2020 | Hayter et al. |
| 10,688,241 B2 | 6/2020 | Yang |
| 10,688,243 B2 | 6/2020 | Cabiri |
| 10,688,294 B2 | 6/2020 | Cowan et al. |
| 10,709,834 B2 | 7/2020 | Chiu et al. |
| 10,716,891 B2 | 7/2020 | Saab et al. |
| 10,716,893 B2 | 7/2020 | Gray et al. |
| 10,716,895 B2 | 7/2020 | Brewer et al. |
| 10,716,896 B2 | 7/2020 | O'Connor et al. |
| 10,716,926 B2 | 7/2020 | Burton et al. |
| 10,719,584 B2 | 7/2020 | Drew |
| 10,722,640 B2 | 7/2020 | McLaughlin |
| 10,722,643 B2 | 7/2020 | Gray et al. |
| 10,722,646 B2 | 7/2020 | Cole et al. |
| 10,722,647 B2 | 7/2020 | Gray |
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,729,849 B2 | 8/2020 | Finan et al. |
| 10,737,015 B2 | 8/2020 | Estes |
| 10,737,016 B2 | 8/2020 | Smith et al. |

(56) References Cited

U.S. PATENT DOCUMENTS

| | | |
|---|---|---|
| 10,737,021 B2 | 8/2020 | Deck |
| 10,737,022 B2 | 8/2020 | Mou et al. |
| 10,737,024 B2 | 8/2020 | Schmid |
| 10,737,026 B2 | 8/2020 | Teutsch |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,751,476 B2 | 8/2020 | Gazeley et al. |
| 10,751,478 B2 | 8/2020 | Nazzaro |
| 10,757,219 B2 | 8/2020 | Moskal |
| 10,758,675 B2 | 9/2020 | Mazlish et al. |
| 10,758,683 B2 | 9/2020 | Gibson et al. |
| 10,758,721 B2 | 9/2020 | Sonderegger et al. |
| 10,765,801 B2 | 9/2020 | McCullough |
| 10,765,803 B2 | 9/2020 | Gonnelli |
| 10,765,807 B2 | 9/2020 | Allis et al. |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,217 B2 | 9/2020 | Nazzaro et al. |
| 10,780,220 B2 | 9/2020 | Gray |
| 10,780,223 B2 | 9/2020 | Desborough et al. |
| 10,792,419 B2 | 10/2020 | Kamen et al. |
| 10,792,424 B2 | 10/2020 | Sasaki |
| 10,792,425 B2 | 10/2020 | Joseph et al. |
| 10,792,440 B2 | 10/2020 | Mandro et al. |
| 10,799,630 B2 | 10/2020 | McCullough |
| 10,799,631 B2 | 10/2020 | Barmaimon et al. |
| 10,799,632 B2 | 10/2020 | Kohlbrecher |
| 10,806,851 B2 | 10/2020 | Rosinko |
| 10,806,854 B2 | 10/2020 | O'Connor et al. |
| 10,806,855 B2 | 10/2020 | Destefano et al. |
| 10,806,859 B2 | 10/2020 | Desborough et al. |
| 10,814,061 B2 | 10/2020 | Bene et al. |
| 10,814,062 B2 | 10/2020 | Gyory |
| 11,136,971 B2 | 10/2021 | Kamen et al. |
| 11,136,972 B2 | 10/2021 | Kamen et al. |
| 11,141,530 B2 | 10/2021 | Moberg et al. |
| 11,261,858 B2 | 3/2022 | Kamen et al. |
| 11,293,425 B2 | 4/2022 | Kamen et al. |
| 11,339,774 B2 | 5/2022 | Gray et al. |
| 2003/0187394 A1 | 10/2003 | Wilkinson et al. |
| 2004/0158207 A1* | 8/2004 | Hunn ............... A61M 39/02 604/164.01 |
| 2005/0065466 A1 | 3/2005 | Vedrine |
| 2006/0106346 A1 | 5/2006 | Sullivan et al. |
| 2007/0124002 A1 | 5/2007 | Estes et al. |
| 2007/0191770 A1 | 8/2007 | Moberg et al. |
| 2008/0215035 A1 | 9/2008 | Yodfat et al. |
| 2008/0234630 A1 | 9/2008 | Iddan et al. |
| 2009/0326453 A1 | 12/2009 | Adams et al. |
| 2010/0049128 A1 | 2/2010 | McKenzie et al. |
| 2010/0094251 A1 | 4/2010 | Estes |
| 2010/0135831 A1 | 6/2010 | Jacobsen |
| 2010/0145303 A1 | 6/2010 | Yodfat et al. |
| 2010/0168670 A1 | 7/2010 | Srisathapat et al. |
| 2010/0241103 A1 | 9/2010 | Kraft et al. |
| 2011/0040247 A1 | 2/2011 | Mandro et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0313357 A1 | 12/2011 | Skutnik et al. |
| 2012/0078170 A1 | 3/2012 | Smith et al. |
| 2012/0136300 A1 | 5/2012 | Schoonmaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | O'Connor et al. |
| 2013/0138075 A1 | 5/2013 | Lambert |
| 2013/0226138 A1 | 8/2013 | Sia |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0052096 A1 | 2/2014 | Searle et al. |
| 2014/0054883 A1 | 2/2014 | Lanigan et al. |
| 2014/0127048 A1 | 5/2014 | Diianni et al. |
| 2014/0128815 A1 | 5/2014 | Cabiri et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0051750 A1 | 2/2016 | Tsoukalis |
| 2016/0074578 A1 | 3/2016 | Xu et al. |
| 2016/0082182 A1 | 3/2016 | Gregory et al. |
| 2016/0089056 A1 | 3/2016 | Limaye et al. |
| 2016/0089524 A1 | 3/2016 | Anderson |
| 2016/0144105 A1 | 5/2016 | Hooven et al. |
| 2016/0193407 A1 | 7/2016 | Qin et al. |
| 2016/0346469 A1 | 12/2016 | Shubinsky et al. |
| 2017/0080157 A1 | 3/2017 | Cabiri et al. |
| 2017/0100542 A1 | 4/2017 | Norton et al. |
| 2017/0232191 A1 | 8/2017 | Smith et al. |
| 2017/0258987 A1 | 9/2017 | Caspers |
| 2017/0290971 A1 | 10/2017 | Hedmann et al. |
| 2017/0296741 A1 | 10/2017 | Gregory |
| 2017/0296742 A1 | 10/2017 | Stefanov |
| 2017/0340827 A1 | 11/2017 | Nazzaro et al. |
| 2017/0340841 A1 | 11/2017 | Sasaki |
| 2017/0351841 A1 | 12/2017 | Moskal |
| 2017/0351851 A1 | 12/2017 | Wang et al. |
| 2017/0368260 A1 | 12/2017 | McCullough et al. |
| 2018/0008768 A1 | 1/2018 | Prescher et al. |
| 2018/0028744 A1 | 2/2018 | Kim |
| 2018/0036476 A1 | 2/2018 | McCullough et al. |
| 2018/0071450 A1 | 3/2018 | Ruhland |
| 2018/0110420 A1 | 4/2018 | Pekander |
| 2018/0185573 A1 | 7/2018 | Niklaus |
| 2018/0193563 A1 | 7/2018 | Krasnow et al. |
| 2018/0200434 A1 | 7/2018 | Mazlish et al. |
| 2018/0200440 A1 | 7/2018 | Mazlish et al. |
| 2018/0207360 A1 | 7/2018 | Juretich et al. |
| 2018/0214635 A1 | 8/2018 | Raman et al. |
| 2018/0221571 A1 | 8/2018 | Carbone et al. |
| 2018/0228967 A1 | 8/2018 | Hopkins et al. |
| 2018/0271455 A1 | 9/2018 | Zhong et al. |
| 2018/0280607 A1 | 10/2018 | Richards et al. |
| 2018/0280608 A1 | 10/2018 | Gillett et al. |
| 2018/0280619 A1 | 10/2018 | Finan et al. |
| 2018/0291882 A1 | 10/2018 | Algawi et al. |
| 2018/0296757 A1 | 10/2018 | Finan et al. |
| 2018/0344926 A1 | 12/2018 | Brandenburg et al. |
| 2018/0361061 A1 | 12/2018 | Andretta |
| 2018/0372085 A1 | 12/2018 | Velschow et al. |
| 2019/0009019 A1 | 1/2019 | Shor et al. |
| 2019/0009022 A1 | 1/2019 | Oakes |
| 2019/0009023 A1 | 1/2019 | Diperna et al. |
| 2019/0015585 A1 | 1/2019 | Smith |
| 2019/0022317 A1 | 1/2019 | Uddin et al. |
| 2019/0060562 A1 | 2/2019 | Olivas et al. |
| 2019/0083057 A1 | 3/2019 | Saul et al. |
| 2019/0083702 A1 | 3/2019 | Nekouzadeh et al. |
| 2019/0091404 A1 | 3/2019 | Nazzaro et al. |
| 2019/0091417 A1 | 3/2019 | McCaffrey et al. |
| 2019/0111202 A1 | 4/2019 | Falkovich |
| 2019/0117896 A1 | 4/2019 | Booth et al. |
| 2019/0117897 A1 | 4/2019 | Avery et al. |
| 2019/0125226 A1 | 5/2019 | Koya et al. |
| 2019/0175828 A1 | 6/2019 | List et al. |

(56) References Cited

U.S. PATENT DOCUMENTS

| | | |
|---|---|---|
| 2019/0262535 A1 | 8/2019 | Shubinsky et al. |
| 2019/0275243 A1 | 9/2019 | Deck et al. |
| 2019/0275249 A1 | 9/2019 | von Campenhausen |
| 2019/0282751 A1 | 9/2019 | Della Bidia |
| 2019/0290845 A1 | 9/2019 | List |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298916 A1 | 10/2019 | List |
| 2019/0298918 A1 | 10/2019 | Jallon |
| 2019/0298921 A1 | 10/2019 | Stafford |
| 2019/0298925 A1 | 10/2019 | Cowe et al. |
| 2019/0307943 A1 | 10/2019 | Franano et al. |
| 2019/0307952 A1 | 10/2019 | Butler et al. |
| 2019/0307954 A1 | 10/2019 | Klemm et al. |
| 2019/0307955 A1 | 10/2019 | Levesque et al. |
| 2019/0307970 A1 | 10/2019 | Kamen et al. |
| 2019/0314572 A1 | 10/2019 | Yang |
| 2019/0321260 A1 | 10/2019 | Grant et al. |
| 2019/0321544 A1 | 10/2019 | List |
| 2019/0321545 A1 | 10/2019 | Saint |
| 2019/0321546 A1 | 10/2019 | Michaud et al. |
| 2019/0321548 A1 | 10/2019 | Cowan |
| 2019/0321552 A1 | 10/2019 | DiPerna et al. |
| 2019/0328963 A1 | 10/2019 | Wolff et al. |
| 2019/0336078 A1 | 11/2019 | Dang et al. |
| 2019/0336678 A1 | 11/2019 | Rule |
| 2019/0336679 A1 | 11/2019 | Staub et al. |
| 2019/0336681 A1 | 11/2019 | Kamen et al. |
| 2019/0336683 A1 | 11/2019 | O'Connor et al. |
| 2019/0341149 A1 | 11/2019 | Chiu et al. |
| 2019/0343434 A1 | 11/2019 | Varsavsky et al. |
| 2019/0344009 A1 | 11/2019 | Damiano et al. |
| 2019/0344010 A1 | 11/2019 | Pizzochero et al. |
| 2019/0344057 A1 | 11/2019 | Cima et al. |
| 2019/0350501 A1 | 11/2019 | Blomquist et al. |
| 2019/0351131 A1 | 11/2019 | Butterfield et al. |
| 2019/0351132 A1 | 11/2019 | Pippin et al. |
| 2019/0351133 A1 | 11/2019 | Grant, Jr. et al. |
| 2019/0351134 A1 | 11/2019 | Cook et al. |
| 2019/0351135 A1 | 11/2019 | Naftalovitz et al. |
| 2019/0351138 A1 | 11/2019 | Bhandar et al. |
| 2019/0351143 A1 | 11/2019 | Egloff et al. |
| 2019/0351209 A1 | 11/2019 | Butziger et al. |
| 2019/0358393 A1 | 11/2019 | Marbet |
| 2019/0358395 A1 | 11/2019 | Olson et al. |
| 2019/0358437 A1 | 11/2019 | Schwartz et al. |
| 2019/0365282 A1 | 12/2019 | Gibson |
| 2019/0365985 A1 | 12/2019 | Zidon et al. |
| 2019/0365986 A1 | 12/2019 | Coiner et al. |
| 2019/0365987 A1 | 12/2019 | Gibson et al. |
| 2019/0365993 A1 | 12/2019 | Staub et al. |
| 2019/0366002 A1 | 12/2019 | Verlaak et al. |
| 2019/0366011 A1 | 12/2019 | Ring |
| 2019/0366012 A1 | 12/2019 | Gross et al. |
| 2019/0368484 A1 | 12/2019 | Chappel et al. |
| 2019/0374434 A1 | 12/2019 | Kamdar et al. |
| 2019/0374706 A1 | 12/2019 | Cabiri et al. |
| 2019/0374707 A1 | 12/2019 | Damestani et al. |
| 2019/0374708 A1 | 12/2019 | Cardinali et al. |
| 2019/0374709 A1 | 12/2019 | Cole et al. |
| 2019/0374711 A1 | 12/2019 | Deliwala |
| 2019/0374714 A1 | 12/2019 | Rioux et al. |
| 2019/0374719 A1 | 12/2019 | Cabiri et al. |
| 2019/0374757 A1 | 12/2019 | Verhoeven et al. |
| 2019/0381238 A1 | 12/2019 | Stonecipher et al. |
| 2019/0381239 A1 | 12/2019 | Cabiri et al. |
| 2019/0381241 A1 | 12/2019 | Bryant et al. |
| 2019/0388609 A1 | 12/2019 | Lanigan et al. |
| 2019/0388612 A1 | 12/2019 | Schramm |
| 2019/0388614 A1 | 12/2019 | Gyrn et al. |
| 2019/0388615 A1 | 12/2019 | Sonderegger et al. |
| 2019/0392938 A1 | 12/2019 | Mermet |
| 2020/0001004 A1 | 1/2020 | Kondo |
| 2020/0001005 A1 | 1/2020 | Politis et al. |
| 2020/0001006 A1 | 1/2020 | Pizzochero et al. |
| 2020/0001007 A1 | 1/2020 | Miesel et al. |
| 2020/0009315 A1 | 1/2020 | Brouet et al. |
| 2020/0009317 A1 | 1/2020 | Cronenberg et al. |
| 2020/0009318 A1 | 1/2020 | Kamen et al. |
| 2020/0009319 A1 | 1/2020 | Ludolph |
| 2020/0009324 A1 | 1/2020 | Barrows et al. |
| 2020/0009331 A1 | 1/2020 | Kamen et al. |
| 2020/0016328 A1 | 1/2020 | Cane' et al. |
| 2020/0016329 A1 | 1/2020 | Schabbach et al. |
| 2020/0016330 A1 | 1/2020 | Kapas et al. |
| 2020/0016333 A1 | 1/2020 | Soares et al. |
| 2020/0016335 A1 | 1/2020 | DiPerna et al. |
| 2020/0016336 A1 | 1/2020 | Patek et al. |
| 2020/0023119 A1 | 1/2020 | Barnes et al. |
| 2020/0023121 A1 | 1/2020 | Thomas et al. |
| 2020/0023122 A1 | 1/2020 | McCullough et al. |
| 2020/0023123 A1 | 1/2020 | O'Connor et al. |
| 2020/0023129 A1 | 1/2020 | Day et al. |
| 2020/0025184 A1 | 1/2020 | Gyory |
| 2020/0027541 A1 | 1/2020 | Xavier et al. |
| 2020/0028914 A1 | 1/2020 | Xavier et al. |
| 2020/0030528 A1 | 1/2020 | Burke et al. |
| 2020/0030529 A1 | 1/2020 | DiPerna et al. |
| 2020/0030530 A1 | 1/2020 | Huang et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0030590 A1 | 1/2020 | Buchman et al. |
| 2020/0030592 A1 | 1/2020 | Cheche |
| 2020/0035355 A1 | 1/2020 | Xavier et al. |
| 2020/0038588 A1 | 2/2020 | Varsavsky et al. |
| 2020/0043588 A1 | 2/2020 | Mougiakakou et al. |
| 2020/0046904 A1 | 2/2020 | Schader et al. |
| 2020/0054822 A1 | 2/2020 | Dewey |
| 2020/0054825 A1 | 2/2020 | Kamen et al. |
| 2020/0054826 A1 | 2/2020 | Diianni et al. |
| 2020/0054832 A1 | 2/2020 | Jeong et al. |
| 2020/0061285 A1 | 2/2020 | Reeves |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0069871 A1 | 3/2020 | Yavorsky et al. |
| 2020/0069873 A1 | 3/2020 | Pizzochero et al. |
| 2020/0069875 A1 | 3/2020 | Nazzaro et al. |
| 2020/0077340 A1 | 3/2020 | Kruse |
| 2020/0077948 A1 | 3/2020 | Schmid |
| 2020/0078511 A1 | 3/2020 | Focht et al. |
| 2020/0078513 A1 | 3/2020 | Wei |
| 2020/0086041 A1 | 3/2020 | Fuchs et al. |
| 2020/0086042 A1 | 3/2020 | Kamen et al. |
| 2020/0086043 A1 | 3/2020 | Saint |
| 2020/0086044 A1 | 3/2020 | Streit et al. |
| 2020/0086045 A1 | 3/2020 | Azapagic et al. |
| 2020/0086051 A1 | 3/2020 | Grygus et al. |
| 2020/0093980 A1 | 3/2020 | McDermott et al. |
| 2020/0093984 A1 | 3/2020 | Shor et al. |
| 2020/0098463 A1 | 3/2020 | Arunachalam et al. |
| 2020/0098464 A1 | 3/2020 | Velado et al. |
| 2020/0101218 A1 | 4/2020 | Shapley et al. |
| 2020/0101219 A1 | 4/2020 | Wang et al. |
| 2020/0101222 A1 | 4/2020 | Lintereur et al. |
| 2020/0101223 A1 | 4/2020 | Lintereur et al. |
| 2020/0101224 A1 | 4/2020 | Lintereur et al. |
| 2020/0101225 A1 | 4/2020 | O'Connor et al. |
| 2020/0101226 A1 | 4/2020 | Rosinko et al. |
| 2020/0108201 A1 | 4/2020 | Ben-David et al. |
| 2020/0108204 A1 | 4/2020 | Mazlish et al. |
| 2020/0111556 A1 | 4/2020 | Schmidlin et al. |
| 2020/0113515 A1 | 4/2020 | O'Connor et al. |
| 2020/0114064 A1 | 4/2020 | Reeves |
| 2020/0114068 A1 | 4/2020 | Schmidlin et al. |
| 2020/0114069 A1 | 4/2020 | Searle et al. |
| 2020/0114072 A1 | 4/2020 | Addiego et al. |
| 2020/0114075 A1 | 4/2020 | Morrow et al. |
| 2020/0114076 A1 | 4/2020 | Ulrich et al. |
| 2020/0114080 A1 | 4/2020 | Barmaimon et al. |
| 2020/0118676 A1 | 4/2020 | Spohn et al. |
| 2020/0121848 A1 | 4/2020 | Schmidlin et al. |

(56) References Cited

U.S. PATENT DOCUMENTS

| | | |
|---|---|---|
| 2020/0121849 A1 | 4/2020 | Christenson et al. |
| 2020/0121850 A1 | 4/2020 | Christenson et al. |
| 2020/0121854 A1 | 4/2020 | Norton et al. |
| 2020/0121937 A1 | 4/2020 | Yoder et al. |
| 2020/0129692 A1 | 4/2020 | Kim et al. |
| 2020/0135323 A1 | 4/2020 | Bazargan |
| 2020/0138852 A1 | 5/2020 | Chattaraj et al. |
| 2020/0138911 A1 | 5/2020 | Joseph et al. |
| 2020/0139137 A1 | 5/2020 | Crawford |
| 2020/0146938 A1 | 5/2020 | Bourelle et al. |
| 2020/0147298 A1 | 5/2020 | Traverso et al. |
| 2020/0147303 A1 | 5/2020 | Lee |
| 2020/0147304 A1 | 5/2020 | Crouther et al. |
| 2020/0147305 A1 | 5/2020 | Estes |
| 2020/0147309 A1 | 5/2020 | Quinn et al. |
| 2020/0155755 A1 | 5/2020 | Chaves et al. |
| 2020/0155757 A1 | 5/2020 | Gregory et al. |
| 2020/0155758 A1 | 5/2020 | Reeves |
| 2020/0164142 A1 | 5/2020 | Poetschke |
| 2020/0164143 A1 | 5/2020 | Cardinali et al. |
| 2020/0164159 A1 | 5/2020 | Chattaraj et al. |
| 2020/0164199 A1 | 5/2020 | Gerlach et al. |
| 2020/0168316 A1 | 5/2020 | Kamen |
| 2020/0171236 A1 | 6/2020 | McCullough et al. |
| 2020/0171294 A1 | 6/2020 | Turner et al. |
| 2020/0179592 A1 | 6/2020 | Adams et al. |
| 2020/0179594 A1 | 6/2020 | Yodfat et al. |
| 2020/0179595 A1 | 6/2020 | McDermott et al. |
| 2020/0179596 A1 | 6/2020 | Dechelette et al. |
| 2020/0179598 A1 | 6/2020 | Penake et al. |
| 2020/0179602 A1 | 6/2020 | Mazlish |
| 2020/0179603 A1 | 6/2020 | Rosinko |
| 2020/0179604 A1 | 6/2020 | Friedli |
| 2020/0179610 A1 | 6/2020 | Bar-El et al. |
| 2020/0188578 A1 | 6/2020 | Bar-El et al. |
| 2020/0188580 A1 | 6/2020 | Gregory et al. |
| 2020/0188581 A1 | 6/2020 | Diianni et al. |
| 2020/0188585 A1 | 6/2020 | Petisce et al. |
| 2020/0188587 A1 | 6/2020 | Sluggett et al. |
| 2020/0188588 A1 | 6/2020 | Estes |
| 2020/0188608 A1 | 6/2020 | Yigal et al. |
| 2020/0197600 A1 | 6/2020 | Chow et al. |
| 2020/0197603 A1 | 6/2020 | Cowe et al. |
| 2020/0197604 A1 | 6/2020 | Friedli |
| 2020/0197621 A1 | 6/2020 | Quinn et al. |
| 2020/0197628 A1 | 6/2020 | McCullough et al. |
| 2020/0206417 A1 | 7/2020 | Yodfat et al. |
| 2020/0206418 A1 | 7/2020 | Gonnelli et al. |
| 2020/0206422 A1 | 7/2020 | Cassim |
| 2020/0206429 A1 | 7/2020 | Hering et al. |
| 2020/0214625 A1 | 7/2020 | Hooven et al. |
| 2020/0215264 A1 | 7/2020 | Searle et al. |
| 2020/0215273 A1 | 7/2020 | Gibson et al. |
| 2020/0222624 A1 | 7/2020 | Destefano et al. |
| 2020/0222625 A1 | 7/2020 | Cabiri et al. |
| 2020/0230313 A1 | 7/2020 | Mojarrad et al. |
| 2020/0230314 A1 | 7/2020 | Kondo et al. |
| 2020/0238003 A1 | 7/2020 | Yigal et al. |
| 2020/0238004 A1 | 7/2020 | McCullough |
| 2020/0238006 A1 | 7/2020 | Groszmann et al. |
| 2020/0238012 A1 | 7/2020 | Bar-El et al. |
| 2020/0246537 A1 | 8/2020 | Bazargan et al. |
| 2020/0246538 A1 | 8/2020 | Bar-El et al. |
| 2020/0246541 A1 | 8/2020 | Neftel et al. |
| 2020/0253632 A1 | 8/2020 | Chong et al. |
| 2020/0254172 A1 | 8/2020 | Forster et al. |
| 2020/0254173 A1 | 8/2020 | McCullough et al. |
| 2020/0254174 A1 | 8/2020 | Kruse et al. |
| 2020/0254175 A1 | 8/2020 | Roy et al. |
| 2020/0254176 A1 | 8/2020 | Rytz et al. |
| 2020/0261002 A1 | 8/2020 | Pace |
| 2020/0261642 A1 | 8/2020 | Ben-David et al. |
| 2020/0261643 A1 | 8/2020 | Boyaval et al. |
| 2020/0261644 A1 | 8/2020 | Farnan et al. |
| 2020/0261645 A1 | 8/2020 | Kamen et al. |
| 2020/0261649 A1 | 8/2020 | Michaud et al. |
| 2020/0261658 A1 | 8/2020 | Farris et al. |
| 2020/0268962 A1 | 8/2020 | Gamelin |
| 2020/0268965 A1 | 8/2020 | Loudermilk et al. |
| 2020/0268975 A1 | 8/2020 | Kim et al. |
| 2020/0272310 A1 | 8/2020 | Vik et al. |
| 2020/0276384 A1 | 9/2020 | Cabiri et al. |
| 2020/0276386 A1 | 9/2020 | Kamen et al. |
| 2020/0282131 A1 | 9/2020 | Nazzaro |
| 2020/0289743 A1 | 9/2020 | Chiu et al. |
| 2020/0289745 A1 | 9/2020 | Harris et al. |
| 2020/0289748 A1 | 9/2020 | Lanigan et al. |
| 2020/0297920 A1 | 9/2020 | McLaughlin |
| 2020/0297923 A1 | 9/2020 | Montalvo et al. |
| 2020/0297927 A1 | 9/2020 | Conrath et al. |
| 2020/0306444 A1 | 10/2020 | Politis et al. |
| 2020/0306445 A1 | 10/2020 | Michaud et al. |
| 2020/0306446 A1 | 10/2020 | Kamen et al. |
| 2020/0306448 A1 | 10/2020 | Schmid |
| 2020/0316290 A1 | 10/2020 | Bourelle et al. |
| 2020/0316291 A1 | 10/2020 | Gibson et al. |
| 2020/0316314 A1 | 10/2020 | Buri et al. |
| 2020/0321094 A1 | 10/2020 | Saint et al. |
| 2020/0324042 A1 | 10/2020 | King et al. |
| 2020/0324048 A1 | 10/2020 | O'Connor et al. |
| 2020/0324101 A1 | 10/2020 | Hartmann et al. |
| 2020/0330679 A1 | 10/2020 | Cronenberg et al. |
| 2020/0330680 A1 | 10/2020 | Deck |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338264 A1 | 10/2020 | Allis et al. |
| 2020/0338266 A1 | 10/2020 | Estes |
| 2021/0060241 A1 | 3/2021 | Kamen et al. |
| 2021/0180583 A1 | 6/2021 | Gray |
| 2021/0180584 A1 | 6/2021 | Kamen et al. |
| 2021/0190063 A1 | 6/2021 | Gray |
| 2021/0270255 A1 | 9/2021 | Gray |
| 2021/0293232 A1 | 9/2021 | Kamen et al. |
| 2021/0321914 A1 | 10/2021 | Brister et al. |
| 2021/0396221 A1 | 12/2021 | Kamen et al. |

FOREIGN PATENT DOCUMENTS

| | | |
|---|---|---|
| EP | 2995330 B1 | 12/2021 |
| EP | 3964249 A1 | 3/2022 |
| WO | 2010051079 A2 | 5/2010 |
| WO | 2010084268 A1 | 7/2010 |
| WO | 2015094945 A1 | 6/2015 |
| WO | 2018129519 A1 | 7/2018 |
| WO | 2018210972 A1 | 11/2018 |
| WO | 2018215465 A1 | 11/2018 |
| WO | 2018218082 A1 | 11/2018 |
| WO | 2018222521 A1 | 12/2018 |
| WO | 2018232171 A1 | 12/2018 |
| WO | 2019018838 A1 | 1/2019 |
| WO | 2019022950 A1 | 1/2019 |
| WO | 2019022951 A1 | 1/2019 |
| WO | 2019038751 A1 | 2/2019 |
| WO | 2019043702 A1 | 3/2019 |
| WO | 2019067386 A1 | 4/2019 |
| WO | 2019070472 A1 | 4/2019 |
| WO | 2019074579 A1 | 4/2019 |
| WO | 2019079868 A1 | 5/2019 |
| WO | 2019081947 A1 | 5/2019 |
| WO | 2019186375 A1 | 10/2019 |
| WO | 2019191222 A1 | 10/2019 |
| WO | 2019193089 A1 | 10/2019 |
| WO | 2019197360 A1 | 10/2019 |
| WO | 2019197361 A1 | 10/2019 |
| WO | 2019200198 A1 | 10/2019 |
| WO | 2019213218 A1 | 11/2019 |
| WO | 2019228895 A1 | 12/2019 |
| WO | 2019229686 A1 | 12/2019 |
| WO | 2020005107 A1 | 1/2020 |
| WO | 2020008017 A1 | 1/2020 |
| WO | 2020011572 A1 | 1/2020 |
| WO | 2020012132 A1 | 1/2020 |

(56) References Cited

FOREIGN PATENT DOCUMENTS

| | | |
|---|---|---|
| WO | 2020012308 A1 | 1/2020 |
| WO | 2020013691 A1 | 1/2020 |
| WO | 2020016172 A1 | 1/2020 |
| WO | 2020025484 A1 | 2/2020 |
| WO | 2020028009 A1 | 2/2020 |
| WO | 2020043459 A1 | 3/2020 |
| WO | 2020046889 A1 | 3/2020 |
| WO | 2020052723 A1 | 3/2020 |
| WO | 2020055785 A1 | 3/2020 |
| WO | 2020068623 A1 | 4/2020 |
| WO | 2020069926 A1 | 4/2020 |
| WO | 2020072233 A1 | 4/2020 |
| WO | 2020072234 A1 | 4/2020 |
| WO | 2020072235 A1 | 4/2020 |
| WO | 2020074988 A1 | 4/2020 |
| WO | 2020075042 A1 | 4/2020 |
| WO | 2020104872 A1 | 5/2020 |
| WO | 2020109409 A1 | 6/2020 |
| WO | 2020109417 A1 | 6/2020 |
| WO | 2020112515 A1 | 6/2020 |
| WO | 2020118165 A1 | 6/2020 |
| WO | 2020120511 A1 | 6/2020 |
| WO | 2020127181 A1 | 6/2020 |
| WO | 2020141412 A1 | 7/2020 |
| WO | 2020144270 A1 | 7/2020 |
| WO | 2020146306 A1 | 7/2020 |
| WO | 2020148581 A1 | 7/2020 |
| WO | 2020160822 A1 | 8/2020 |
| WO | 2020167537 A1 | 8/2020 |
| WO | 2020193090 A1 | 10/2020 |
| WO | 2020197994 A1 | 10/2020 |
| WO | 2020201270 A1 | 10/2020 |

\* cited by examiner

INVISIBLE NEEDLE

This application is a continuation of U.S. patent application Ser. No. 11/519,137, filed on Sep. 11, 2006, which claims the benefit of U.S. Provisional Application No. 60/716,222, filed Sep. 12, 2005, and EP Patent Application No. 05019774.8, filed Sep. 12, 2005, which are incorporated herein by reference in their entireties.

TECHNICAL FIELD

The invention relates to an inserter for an infusion set for intermittent or continuous administration of a therapeutical substance, such as e.g. insulin. The inserter comprises a needle hub comprising an insertion needle and two spring units assuring automatic insertion and automatic retraction of the insertion needle.

BACKGROUND OF THE INVENTION

The document U.S. Pat. No. 6,387,078 pertains to an automatic injection apparatus which injects a single, pre-measured dose of stored medicine intramuscularly or transdermally, and the injection apparatus automatically retracts the hypodermic needle into the device after the injection is completed. The user presses the distal end i.e. the needle end, of the device onto the desired injection site and presses the actuation button. This releases the plunger-syringe-combination from its temporary engagement with the housing. The plunger-syringe-combination together with the spring-to-plunger-coupling are then forced away from the proximal end, i.e. the actuation end, of the housing by an energized driver spring. The driver spring propels the plunger-syringe-combination forward through the bore of the housing until the hypodermic needle exits the housing, and enters the recipient's tissue, and the syringe barrel touches the interior distal end of the housing. During this movement, a return spring positioned between the syringe assembly and the fixed, distal end of the housing becomes compressed and energized. When the liquid of the automatic injection apparatus is discharged by the plunger being pushed forward through the interior of the syringe barrel, the spring-to-plunger-coupling comes into contact with a splitter which disengages the driver spring from the plunger. Without the influence of the driver spring upon the plunger-syringe-combination, the energized return spring forces the plunger-syringe-combination to retreat rearward towards the proximal end of the device until the hypodermic needle is fully retracted into the housing.

As this automatic injection apparatus is directed toward injections of a pre-measured dose of stored liquid medicine where the plunger during injection pushes the liquid dose of stored medicine out of the apparatus, the solution will not be applicable for use when inserting an injection device as the handling and injection of a liquid under sterile conditions necessitates a complicated injection apparatus which need to interact with the liquid.

WO 2005/046780 (FIG. 97-102) describes a device used for automatic insertion of a cannula of an infusion device into the skin of a patient, and afterwards automatic retraction of the insertion needle. The insertion device has the form of an oblong cylinder (length≈4× diameter) which is open in one end (1984) and provided with means for activation at the other end (1952). When the infusion set has been loaded onto the needle (1968) the lock member (1962) is moved in direction of the end provided with means for activation by the patient using projections (1974) which projections are accessible through a slot (1976) of the housing until barbs (1956) of the lock member (1962) engage an outer surface of the housing (page 26, I. 24-27). Then the open end (1984) is placed against the skin of the patient and the means for activation (1952) is activated. When activated shoulders (1954) on the means for activation engage, the barbs (1956) are pushed toward each other in order to disengage the barbs from the housing. When the barbs are clear of the housing the lock member, the needle hub, the retainer body and the associated infusion device are moved by a first spring in direction of the open end (1984). The inserter device moves the infusion device towards the skin of the patient thereby inserting the needle and the cannula of the infusion device. As the cannula is fully inserted, barbs (1964) of the needle hub (1965) engage ramped surfaces (1972) of the sleeve (1982), causing the barbs (1964) to be forced toward one another. When the barbs (1964) have been forced sufficiently inwardly to clear ends (1988) of the main body (1980), the second spring (1966) then moves the needle hub (1965) in the direction of the activation means (1952). Thus the needle is removed from the infusion device leaving the infusion device in place on the skin while the retainer body remains in a position adjacent the open end of the sleeve so that once the insertion device is removed from the skin of the patient, the retainer body protects the patient from further contact with the needle.

This insertion device is rather complex and the length of the device is defined by the individual units forming the functional parts of the device as these units have to be placed more or less end to end. A feature illustrating the complexity of the unit is the fact that the two springs respectively biases the housing from the lock member and the retainer body from the needle hub while a main body is placed between the two spring systems to transfer the force from the first spring to the second spring.

According to the present invention the two spring units work directly together, as the first spring unit directly affects the movement of the carrier body while the second spring system is directly affected by the movement of the carrier body. That the spring units directly affect or is directly affected by the carrier body means that the spring units are connected to the carrier body directly or through a part which transfers the power either unchanged or under controlled modifications.

DESCRIPTION OF INVENTION

The object of the invention is to provide a simple, non-expensive inserter for an infusion device which inserter would be easy and safe for the user to handle during use and safe to dispose of after use.

The invention concerns an inserter for an infusion set comprising a housing, a carrier body carrying an infusion part, a needle hub, a first moving unit bringing the carrier body to a forward position and a second moving unit bringing the carrier body to a retracted position, where the inserter has means for activation which should be activated at least once in order to bring the carrier body from a retracted to a forward position, and back from the forward to the retracted position.

In a preferred embodiment the inserter has means for activation which has to be activated only once in order both to bring the carrier body from a retracted to a forward position, and back from the forward to the retracted position.

Preferably the first moving unit and the second moving unit are placed at least partly parallel to each other, where "parallel" is understood as not being "serially". "Serially"

means that one moving unit is placed in extension of the other as described e.g. in WO 2005/046780. When the moving units are placed at least partly parallel they could be placed beside each other i.e. they extend over the same length or partly over the same length, or one unit could be placed inside the other if e.g. one of the units is of a kind presenting a hollow centre such as a helical spring.

In a preferred embodiment the first moving unit and the second moving unit are placed at least partly parallel to each other inside the housing.

The invention also comprises an inserter for an infusion set comprising a housing, a carrier body carrying an infusion part, a needle hub, a first spring unit and a second spring unit, where
- the housing is provided with guiding means on the internal surface for guiding the movement of the carrier body,
- the needle hub comprises an insertion needle for piercing of the skin,
- the carrier body has a retracted and a forward position, and in the retracted position before insertion the carrier body and the needle hub are locked to each other,
- the carrier body is provided with guiding means corresponding to the guiding means on the housing,
- the first spring unit is biasing the housing and the carrier body and the second spring unit is biasing the carrier body and the needle hub.

In a preferred embodiment the first and the second spring unit are both connected to a distal surface of the carrier body.

In another preferred embodiment the carrier body stays in a forward position after insertion of the needle.

In another preferred embodiment the infusion part is provided with an adhesive proximal surface.

In another preferred embodiment the infusion part is provided with an adhesive distal surface.

In another preferred embodiment an adhesive pad is releasably fastened to a proximal part of the housing, and the adhesive pad can cover a proximal opening of the housing through which the infusion part will be conveyed.

In another preferred embodiment the first spring unit and the second spring unit respectively comprises one compression spring.

In another preferred embodiment the carrier body is provided with at least one inclined surface which surface is in contact with a rotating part of the needle hub, which rotating part can rotate in relation to the main part of the needle hub to which the insertion needle is fastened, and the housing is provided with a member preventing the rotating part of the needle hub from rotating when the carrier body is in a retracted position.

The invention also comprises a method for inserting an infusion part where the infusion part is releasably fastened to a needle hub and the needle hub is releasably fastened to a carrier body which carrier body carries the infusion part from a retracted to a forward position, where
- a biased spring unit activated by the user, moves the carrier body, the needle hub and the infusion part forward from a retracted position, until a proximal surface of the infusion part contacts the patients skin or contacts a part connected to the patients skin;
- at this forward position the needle hub is released from the carrier body and a biased spring unit moves the needle hub away from the carrier body resulting in the retraction of the needle hub; then the infusion part is released from the carrier body and the housing—including the carrier body and the needle hub—is removed from the patient.

DESCRIPTION OF THE DRAWINGS

The invention is explained in greater detail below with reference to the accompanying drawings wherein a preferred embodiment of the invention is shown.

In this document "distal" describes a surface or a part turned away from or placed away from the patient when the inserter is positioned with the needle end toward the patient. "Proximal" describes a surface or a part turned in direction of or placed close to the patient.

Figure 1:
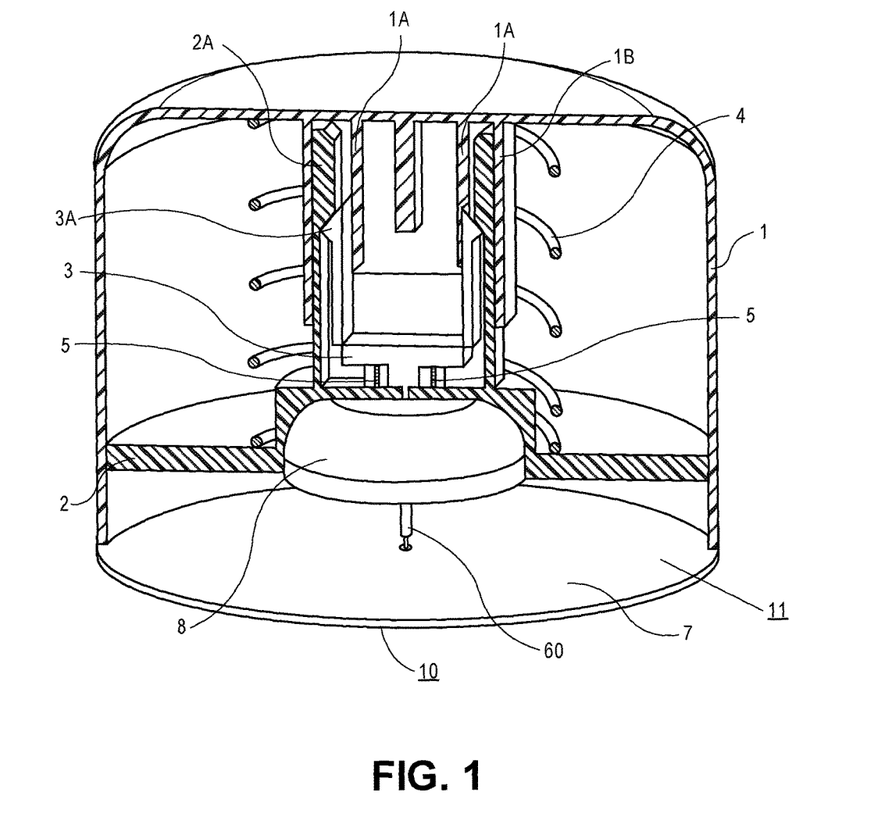
FIG. 1 is a side view of an embodiment of the inserter of the invention where the carrier body and the infusion device are in a retracted position.

The embodiment of the inserter in FIG. 1 has a housing 1 with a length a little smaller than the diameter (length≈1× diameter). The design of this inserter is mainly defined by the use and not by the constructional units inside the inserter. The constructional units of the device are few and small, and the design of the inserter such as size and shape, results from a wish of making the device easy to store and easy to handle for a user, even if the user has reduced dexterity of the hands.

The inserter comprises a carrier body 2 with at least two locking members 2a protruding from a distal surface of the carrier body. A needle hub 3 is placed between the two locking members 2a, and the needle hub is provided with members 3a protruding from a distal surface of the needle hub and corresponding to the locking means 2a of the carrier body 2. These protruding members 3a can rotate towards the center of the device along an axis through which they are also fastened to the main part of the needle hub 3. Further the needle hub is provided with an insertion needle 6 protruding from a proximal surface of the needle hub. Before insertion an infusion part 8 is fastened to the carrier body 2, the infusion part is provided with a cannula which is adjoined to the insertion needle in such a way that insertion of the needle 6 will result in insertion of the cannula. An adhesive pad 7 with an adhesive proximal surface covers the proximal opening of the housing 1. The adhesive surface of the pad 7 will normally be covered with a release liner in order to protect the adhesive surface.

During insertion the needle hub 3 is moved from a retracted position, to a forward position and back to a retracted position by a system of springs. The system in FIG. 1-5 comprises two springs, a first spring 4 and a second spring 5. According to Hooke's law the force exerted by a spring depends on displacement of the spring x and of the spring constant k: $F_{spring} = -k\,x$. Each of the springs 4 and 5 can be replaced by more than one spring, then the spring unit replacing e.g. the first spring 4 shown in FIG. 1-5, would exert the force:

$$F_{spring} = (-k_1)\cdot x_1 + (-k_2)\cdot x_2 + \ldots + (-k_n)\cdot x_n \stackrel{as\ x_1=x_2=x_n}{=} -(k_1+k_2+\ldots+k_n)\cdot x$$

where $k_1, k_2, \ldots, k_n$ are the spring constants for the individual springs, and $F_{spring}=-k\cdot x$, where $k=k_1+k_2+\ldots+k_n$.

The first spring 4 and the second spring 5 can comprise both compression and tension springs.

In the embodiment of FIG. 1-5, the housing 1 is provided with guiding means 1a and 1b. The guiding means 1a and 1b comprises parallel walls, an inner wall 1a and an outer wall 1b, protruding from the distal inner surface of the housing 1. The locking members 2a of the carrier body 2 and the protruding members 3a of the needle hub 3 are placed between the parallel walls 1a and 1b. The locking members 2a have one or more inclined surfaces which are in contact with a part of the protruding members 3a. When the carrier body 2 is pulled or pushed towards the patient's skin, the locking members 2a will exert a force on and perpendicular to each inclined surface. This force has one component parallel to the walls 1a and 1b pointing in same direction as the movement, and another component perpendicular to the first component pointing toward the inner wall 1a. As long as the inner wall 1a is present, a force of same size but opposite direction as the second component will push back from the inner wall 1a keeping the protruding member 3a in a steady position between the walls 1a and 1b. When the inner wall 1a is not present the second component of the force exerted by the locking member will push the protruding members 3a towards the center of the device.

When the protruding members 3 have been released from interlocking with the locking members 2a, the needle hub is not influenced by a force in direction of the infusion part, and the force exerted by the second string 5 will overcome the friction between the insertion needle and the cannula extending from the infusion part 8 and move the needle hub 3 away from the infusion part 8.

In FIG. 1 the carrier body 2 is placed and locked in a retraced position. The insertion needle 6 which is adjoined to the cannula is seen below the infusion part 8. Both the spring units 4 and 5 are biased, and the locking members 2a is interlocked with the protruding members 3a of the needle hub 3 due to support of the inner walls 1a.

When the user wants to insert the infusion device, the device is first placed on the insertion site on the patient. Then the inserter is activated by the user by unlocking the carrier body 2 from the housing 1.

It is not shown on this embodiment how unlocking of the carrier body 2 is done but one way is to provide the carrier body 2 with two members protruding into openings of the housing 1 opposite each other. Unlocking of the carrier body is then performed by the user pressing on the housing 1 at two opposite points placed on a line perpendicular to the line formed by the two protruding members of the carrier body 2. Pressing on the two points on the perpendicular line will cause a deformation of the housing 1 and increase the distance between the two corresponding openings in the housing 1, the protruding members of the carrier body will then be released from the housing 1.

Figure 2:
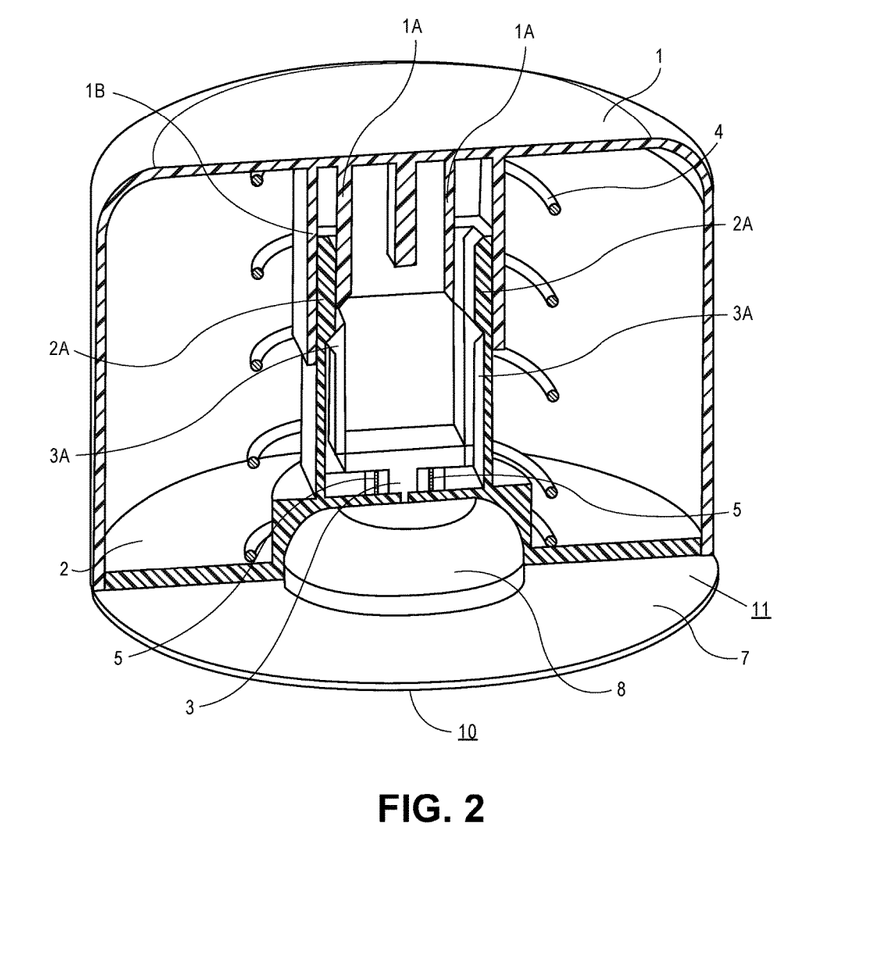
FIG. 2 is a side view of the inserter with the carrier body and the infusion device in an advanced position where the needle hub is locked to the carrier body.
Figure 3:
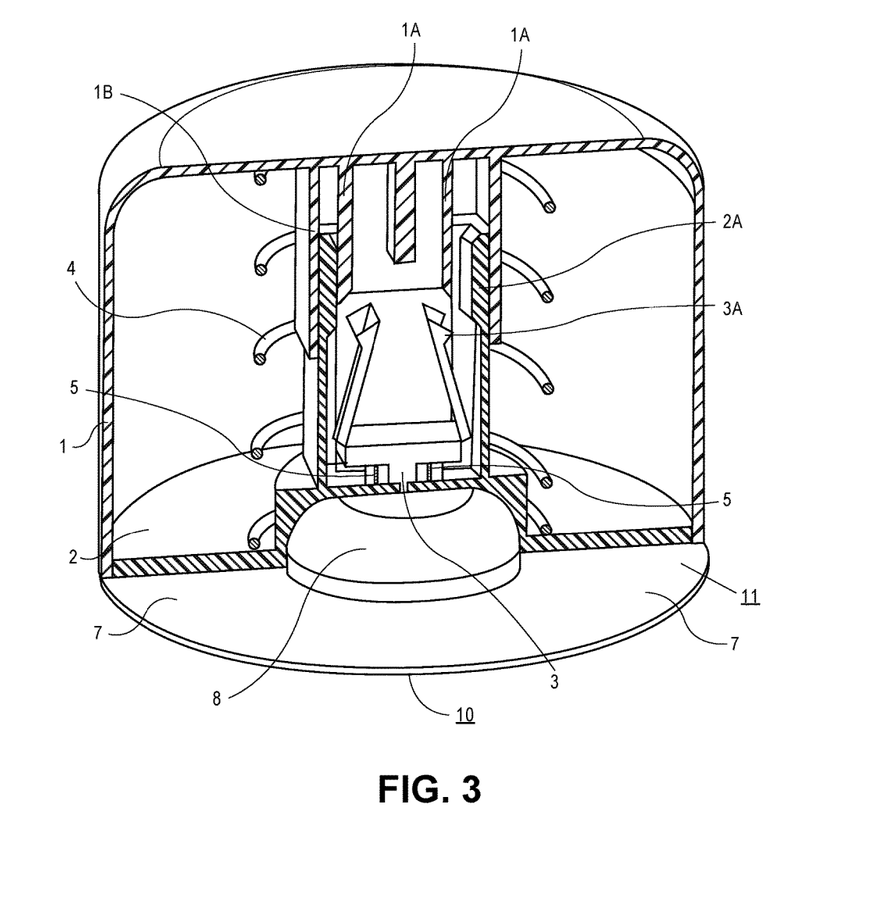
FIG. 3 is a side view of the inserter with the carrier body and the infusion device in an advanced position where the needle hub has been released from the carrier body.

When the inserter is activated the first string 4 tries to return to an unbiased position and doing this brings the carrier body 2 and the infusion part 8 to a forward position shown in FIG. 2.

In this forward position the insertion needle 6 and the adjoined cannula have penetrated the adhesive pad 7 placed at the proximal end of the housing 1. The protruding members 3a of the needle hub 3 have in FIG. 2 been released from the support of the inner walls 1a, and as soon as the release from the inner walls 1a has taken place the protruding members 3a of the needle hub will be forced towards the center of the inserter to the position shown in FIG. 3.

Figure 4:
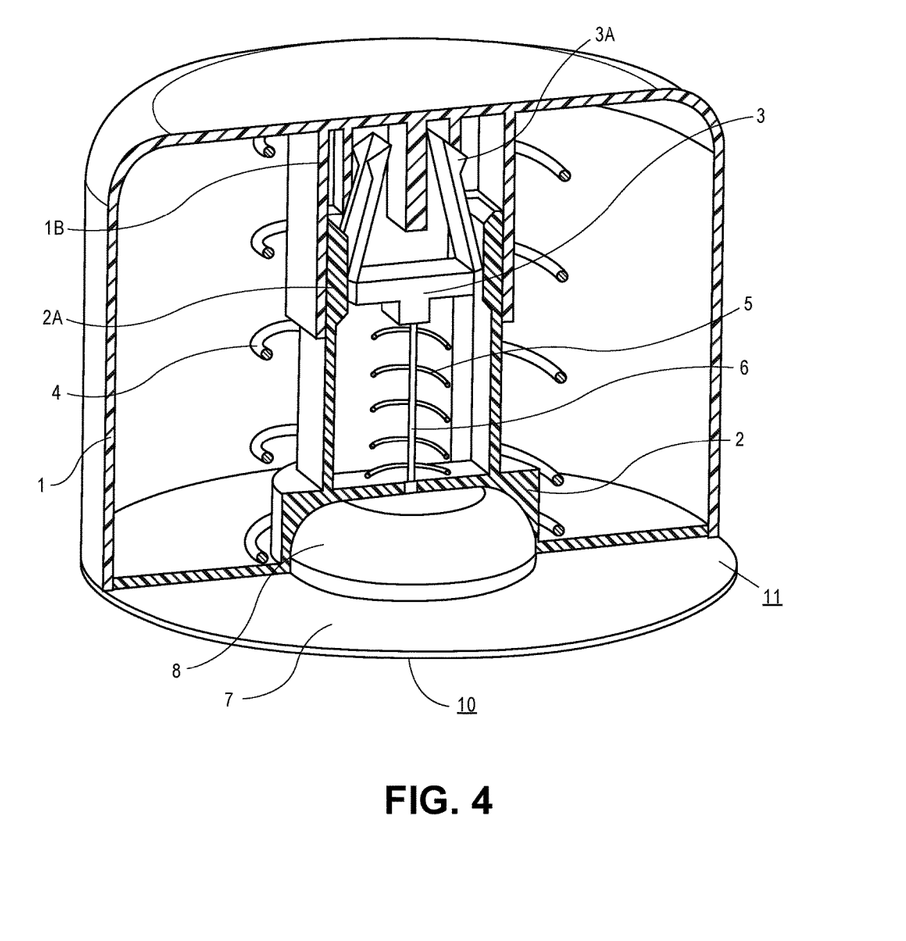
FIG. 4 is a side view of the inserter with the carrier body and the infusion device in an advanced position where the needle hub is in a retracted position.

Immediately after the protruding members 3a of the needle hub are free of the inner walls 1a, the upward force from the spring unit 5 will bring the needle hub 3 to the position shown in FIG. 4, where the needle hub 6 and the insertion needle 6 is fully covered by the housing 1.

Figure 5:
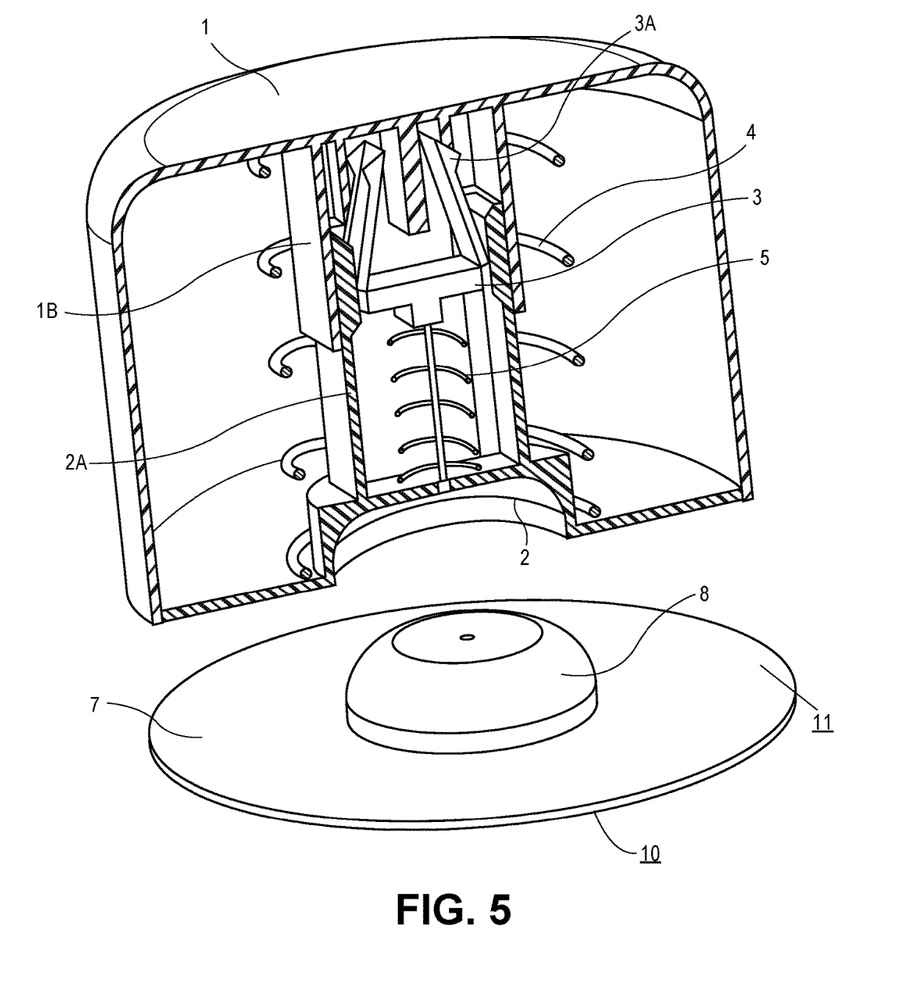
FIG. 5 is a side view of the inserter after the inserter has been removed from the patient leaving the infusion part on the patient's skin.

In FIG. 5 it is shown how the infusion part 8 has been secured to the adhesive pad 7, the pad 7 is secured to the patient, and then the inserter is removed and can be disposed of in a safe way together as the contaminated insertion needle 6 is placed behind the protective walls of the inserter housing 1.

The invention claimed is:

1. An inserter for an infusion set comprising
   a housing;
   an infusion part having a proximal surface adjoined to a cannula;
   a carrier body configured to releasably carry the infusion part and moveable from a carrier body retracted position to a carrier body forward position, wherein the proximal surface of the infusion part is away from a patient's skin when the carrier body is in the carrier body retracted position;
   a needle hub securing an insertion needle, wherein the needle hub is releasably fastened to the carrier body and the infusion part is releasably fastened to the needle hub, wherein the needle hub is moveable from a needle hub retracted position to a needle hub forward position and from the needle hub forward position to the needle hub retracted position, and wherein the insertion needle and the cannula are inserted into the patient's skin when the needle hub is in the needle hub forward position;
   a first moving unit biasing the carrier body to the carrier body forward position when the carrier body is in the carrier body retracted position; and
   a second moving unit biasing the needle hub away from the carrier body and moving at least a portion of the insertion needle inside the housing when the carrier body is in the carrier body forward position.

2. The inserter of claim 1, further comprising an adhesive pad operable to adhere the housing to skin, wherein the adhesive pad comprises an adhesive proximal surface.

3. The inserter of claim 1, wherein the insertion needle extends at least partially through the infusion part before insertion of the insertion needle into the patient's skin.

4. The inserter of claim 1, wherein the carrier body stays in the carrier body forward position after insertion of the insertion needle.

5. The inserter of claim 4, wherein the carrier body stays in the carrier body forward position and the insertion needle is retracted from the patient's skin after insertion of the insertion needle.

6. The inserter of claim 1, wherein the needle hub extends distal to the carrier body within the housing.

7. The inserter of claim 1, wherein the first moving unit and the second moving unit are connected to a distal surface of the carrier body.

8. The inserter of claim 1, wherein the first moving unit and the second moving unit are inside the housing.

9. The inserter of claim 1, wherein the first moving unit comprises a compression spring.

10. The inserter of claim 1, wherein the second moving unit comprises a compression spring.

11. The inserter of claim 1, wherein movement of the first moving unit directly affects movement of the carrier body to the carrier body forward position and movement of the carrier body directly affects movement of the second moving unit.

12. The inserter of claim 1, wherein movement of the second moving unit overcomes the friction between the insertion needle and the cannula and moves the insertion needle and the needle hub away from the infusion part.

13. The inserter of claim 1, wherein the housing comprises an internal surface and guiding members on the internal surface, wherein the guiding members guide movement of the carrier body relative to the housing.

14. The inserter of claim 13, wherein the carrier body comprises locking members corresponding to the guiding members and wherein the locking members engage with the guiding members as the carrier body moves relative to the housing.

15. The inserter of claim 14, wherein the needle hub is placed between the locking members of the carrier body.

16. The inserter of claim 14, wherein the carrier body and the needle hub are locked to each other when carrier body is in the carrier body retracted position.

17. The inserter of claim 14, wherein the carrier body comprises at least one inclined surface and the needle hub comprises a protruding member, wherein the at least one inclined surface is in contact with the protruding member.

18. The inserter of claim 17, wherein the protruding member and the locking members are placed between the guiding members when the carrier body is in the carrier body retracted position.

19. The inserter of claim 17, wherein the locking members exert a force on the at least one inclined surface as the carrier body moves to the carrier body forward position.

20. The inserter of claim 17, wherein the protruding member moves toward center of the housing and away from the at least one inclined surface when the needle hub is in the needle hub forward position.

21. An inserter for an infusion set comprising:
a housing;
an infusion part having a proximal surface adjoined to a cannula;
a carrier body configured to releasably carry the infusion part and moveable from a retracted position to a forward position, wherein the proximal surface of the infusion part is away from a patient's skin when the carrier body is in the retracted position;
an insertion needle, wherein the insertion needle is secured to a needle hub and wherein the insertion needle and the cannula are inserted into the patient's skin when the carrier body is in the forward position;
a first moving unit biasing the carrier body to the forward position when the carrier body is in the retracted position; and
a second moving unit biasing the needle hub away from the carrier body and moving at least a portion of the insertion needle inside the housing when the carrier body is in the forward position,
wherein the first moving unit and the second moving unit are placed at least partly parallel to each other and the second moving unit does not extend beyond first and second ends of the first moving unit when the carrier body is in the retracted position and the forward position.

22. The inserter of claim 21, wherein the needle hub is releasably fastened to the carrier body and the infusion part is releasably fastened to the needle hub.

\* \* \* \* \*